United States Patent [19]

Hamdan et al.

[11] Patent Number: 5,314,820
[45] Date of Patent: May 24, 1994

[54] PROCESS AND MICROORGANISMS FOR PRODUCING SINGLE CELL PROTEIN

[75] Inventors: Ibrahim Y. Hamdan; Amin S. ElNawawy; Ibrahim M. Banat; Nader M. Al-Awadhi, all of Kuwait City, Kuwait

[73] Assignee: Kuwait Institute for Scientific Research, Kuwait City, Kuwait

[21] Appl. No.: 120,322

[22] Filed: Nov. 13, 1987

[51] Int. Cl.$^5$ ............... C12N 1/20; C12P 21/04
[52] U.S. Cl. ............... 435/252.1; 435/252.4; 435/804; 435/71.2
[58] Field of Search ............... 435/252.1, 822, 252.4, 435/804, 71.2

[56] References Cited

U.S. PATENT DOCUMENTS

| | | | |
|---|---|---|---|
| 3,865,691 | 2/1975 | Ridgway et al. | 435/68 |
| 3,981,774 | 9/1976 | Hitzman | 435/68 |
| 3,989,594 | 11/1976 | MacLennan et al. | 435/247 |
| 3,989,595 | 11/1976 | Mateles et al. | 435/68 |
| 4,082,611 | 4/1978 | Cotton | 435/68 |
| 4,145,445 | 3/1979 | Hitzman | 426/60 |
| 4,166,004 | 8/1979 | Prave et al. | 435/822 X |
| 4,302,542 | 11/1981 | Hitzman | 435/247 |
| 4,341,802 | 7/1982 | Hopkins | 426/60 |
| 4,368,271 | 1/1983 | Miura et al. | 435/247 |
| 4,425,432 | 10/1984 | Zeikus et al. | 435/140 |
| 4,439,523 | 3/1984 | Malick et al. | 435/243 |
| 4,652,527 | 3/1987 | Stirling | 435/155 |

OTHER PUBLICATIONS

Dahl, Mehta, and Hoare, *Journal of Bacteriology*, 109, 916-921 (1982).
Dostalek and Molin, *Single Cell Protein II*, 385-401 (1975).
Drozd and Linton, *Continuous Culture of Cells*, 1, 113-141 (1981).
Gaden & Humphrey eds.: *Single Cell Protein from Renewable and Nonrenewable Resources* (1977).
Green and Bousfield, *Journal of General Microbiology*, 128, 623-638 (1982).
Goldberg and Mateles, *Journal of Bacteriology*, 124, 1028-1029 (1975).
Hamer, *Economic Microbiology*, 4, 315-360 (1979).
Hamer and Hamedan, *Chemical Society Reviews*, 8 (No. 1), 143-170 (1979).
Hamdan ed.: *Proceedings of the International Symposium on Single Cell Proteins from Hydrocarbons for Animal Feeding* (1983).
Hamdan, Asthana, Al-Awadi, ElNawawy, Banat and Salman, *Perspectives in Biotechnology and Applied Microbiology*, 49-60 (Nov. 17, 1986).
Hohnloser, Lingens and Präve, *European Journal of Applied Microbiology and Biotechnology*, 6, 167-179 (1978).
Ikemoto, Kotoh and Komagata, *Journal of General and Applied Microbiology*, 24, 41-49 (1978).
Jenkins, Byrom and Jones, *Proceedings, IVth International Symposium on Microbial Growth on $C_1$ Compounds* (1984).

(List continued on next page.)

*Primary Examiner*—Irene Marx
*Attorney, Agent, or Firm*—Willian Brinks Hofer Gilson & Lione

[57] ABSTRACT

A methanol-utilizing bacterium selected from the group consisting of Methylophilus KISRI 5 (NCIB 12135), Methylophilus KISRI 6.1 (NCIB 12136), Methylophilus KISRI 512 (NCIB 12137), Methylophilus KISRI 5112 (NCIB 12138) and mutants and variants thereof. Also, bacterial cultures comprising these novel strains of Methylophilus and a method of producing single cell protein comprising culturing one or more of the Methylophilus strains of the invention in a methanol-containing aqueous culture medium, preferably in the culture medium of the invention which has been optimized for culturing these novel Methylophilus strains. The culture method preferably further comprises the recycling of spent culture medium.

4 Claims, 2 Drawing Sheets

OTHER PUBLICATIONS

Peel and Quayle, *Biochem. J.*, 81, 465–69 (1961).
Prokop, Ratcliff, Fattayer, Al-Awadhi, Khamis, Murad, Bond and Hamdan, *Biotechnology and Bioengineering*, 26, 1085–1089 (1984).
Urakami and Komagata, *Journal of General and Applied Microbiology*, 25, 343–360 (1979).
Urakami and Komagata, *International Journal of Systematic Bacteriology*, 14, 188–201 (1984).
Whittenbury and Krieg, *Bergey's Manual of Systematic Bacteriology*, 259–60 (1983).
*Journal of General Microbiology*, 133, 453–73, (1987), (Jenkins I).
Jenkins et al. (II), *Int. J. Syst. Bact.*, vol. 37, pp. 446–448, 1987.
Anthony, C., "The Biochemistry of Methylotrophs", 1982, Academic Press, pp. 22–27.
Gerhardt et al., "Manual of Methods for General Bacteriology", ASM, 1981, pp. 84–97.
Dalton et al., *Arch. Microbiol.*, vol. 109, 1976, pp. 147–151.

PROCESS AND MICROORGANISMS FOR PRODUCING SINGLE CELL PROTEIN

BACKGROUND OF THE INVENTION

This invention relates to growing bacteria to produce large quantities of single cell protein. More specifically, it relates to a process for efficiently and economically producing large quantities of single cell protein by culturing four novel strains of the genus Methylophilus in an optimized aqueous, methanol-containing culture medium.

As used herein, "single cell protein" is defined to mean an isolated mass of non-viable, dried cells of microorganisms produced by cultivating such microorganisms on substrates such as alkanes, lower hydrocarbons, lower alcohols or industrial and agricultural waste products which is destined to be used as a protein source.

Indigenous food production in many countries of the world does not meet the demand for food in those countries. In particular, due to sparse agricultural resources, food production in the hot, arid regions of North Africa and the Middle East is severely limited. Despite the production of intensive chicken, egg and meat production schemes, food production still does not meet the total consumption requirement. Since these chicken, egg and meat production schemes require protein-containing feeds, the production of single cell protein by growing microorganisms could relieve the foreseen shortage of food, particularly protein, in these countries.

For industrial-scale microbial processes to be used successfully in hot, arid regions, such processes must be capable of being both cooled economically and operated without the requirement for inordinately high quantities of drinking quality water. In addition, the process should have a high level of productivity.

BRIEF DESCRIPTION OF THE INVENTION

Accordingly, it is an object of the invention to provide a process for the production of large quantities of single cell protein which utilizes microorganisms that are robust, stable, non-fastidious and capable of growing efficiently under economic process conditions at high ambient temperatures. It is a further object of the invention to provide a liquid culture medium that is optimized for this process and for the growth of the selected microorganisms. Finally, it is an object of the invention to provide an operating mode comprising a series of process operations (in addition to the fermentation operation) that minimize requirements for the components used in the process, especially the requirement for water. These and other objects are achieved by the present invention.

In a first aspect, the present invention comprises the following four novel strains of bacteria: Methylophilus KISRI 5 (NCIB 12135), Methylophilus KISRI 6.1 (NCIB 12136), methylophilus KISRI 512 (NCIB 12137), Methylophilus KISRI 5112 (NCIB 12138). The invention is also intended to encompass mutants and variants of these strains. Mutants may arise spontaneously or may be induced by methods known in the art. Variants of the microorganisms of the invention may be obtained by using other techniques for manipulating microorganisms, such as genetic engineering techniques, which are also known in the art.

In another aspect, the invention comprises a method for producing single cell protein comprising culturing one or more of the novel Methylophilus strains of the invention in a methanol-containing aqueous culture medium, preferably in a culture medium optimized for culturing the novel Methylophilus strains of the invention. The optimized culture medium is another aspect of the invention, and the exact formula of this medium is set forth below.

During the culturing of the four novel Methylophilus strains of the invention, the temperature is preferably maintained at from about 37° to about 44° C., most preferably from about 38° to about 42° C. A 6% solution of ammonia is used to adjust and maintain the pH at about 6.8. The method of the invention can be carried out batchwise or in a continuous flow mode, although the continuous flow mode is preferred since it allows for the production of large quantities of single cell protein.

The method preferably further includes the recycling of spent culture medium. In particular, the spent culture medium is preferably recycled as follows: the spent culture medium is separated from the bacteria in the culture; the separated spent culture medium is heated at from about 83° to about 87° C.; the heated spent culture medium is then cooled to from about 40° to about 50° C. to precipitate biopolymeric matter; the cooled spent culture medium is filtered to remove the precipitated biopolymeric matter; the filtered spent culture medium is supplemented with nutrients; and one or more of the novel Methylophilus strains of the invention is cultured in a culture medium at least partially comprising the supplemented spent culture medium.

Although the method, medium and bacteria of the invention are particularly adapted for use in hot, arid regions of the world, the invention can, of course, be practiced quite successfully in other parts of the world. The use of the method, medium and bacteria of the invention leads to the production of large quantities of single cell protein, particularly when the method is run in the continuous flow mode. The single cell protein can be used as a source of protein in a variety of animal feeds.

DETAILED DESCRIPTION OF THE INVENTION

Figure 1:
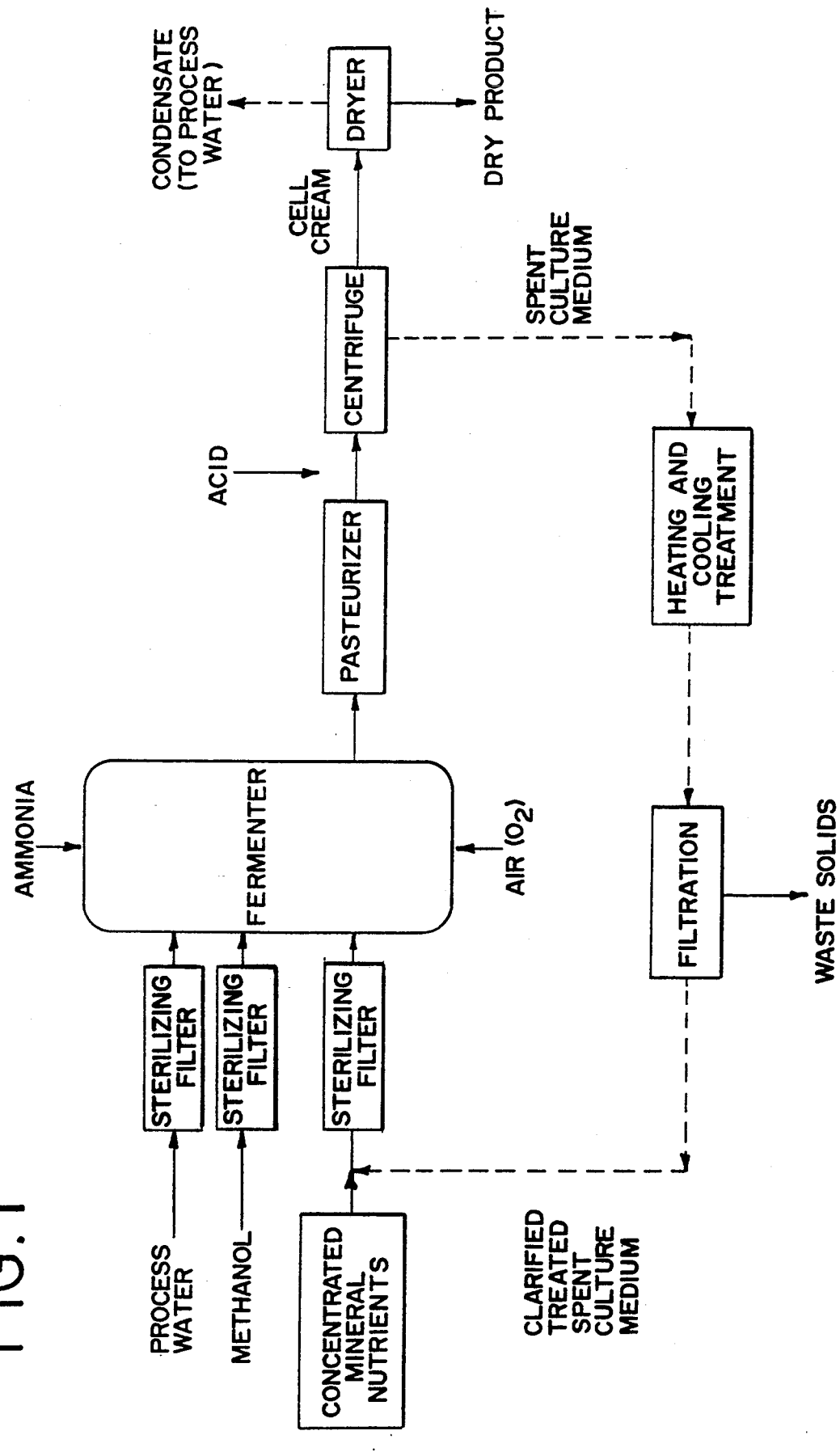
FIG. 1 depicts, in flow-chart form, one embodiment of the method of the invention.

According to the invention, there are provided four novel pure methanol-utilizing bacterial strains. Methanol is widely recognized as one of the most suitable carbon sources for the production of single cell protein. Methanol is also widely available in excess in many of the regions of the world that are facing food shortages. Thus, the four novel bacterial strains of the invention are well-suited to be used in these regions of the world.

The four novel strains of the invention were isolated from a mixed culture originally obtained from Kuwait soil by the continuous enrichment technique at 45° C. They were purified using both the dilution pour-plate and streaking techniques on methanol-containing solid media plates. Discrete colonies obtained were repeatedly further streaked to ensure their purification before being subjected to a large number of morphological and biochemical tests.

The four novel strains of the invention were deposited at the National Collection of Industrial and Marine Bacteria (NCIMB), Torry Research Station, P.O. Box No. 31, 135 Abbey Road, Aberdeen, AB9 8DG, Scotland, on Aug. 7, 1985. They were given the following accession numbers:

| DESIGNATION OF THE INVENTORS | NCIMB ACCESSION NUMBER |
|---|---|
| KISRI 5 | NCIB 12135 |
| KISRI 6.1 | NCIB 12136 |
| KISRI 512 | NCIB 12137 |
| KISRI 5112 | NCIB 12138 |

Each culture was subjected to a large number of tests typical of those used for identifying new and existing strains of bacteria, including: morphological (4); cultural (14); sugar fermentation (17); nitrogen source utilization (8); carbon source assimilation (71); enzyme activity (19); biochemical (16); antibiotic sensitivity (21); specific media growth (7); growth at different pH (6); and growth at different temperatures (6) (the numbers in brackets are the number of the different tests carried out in eachcategory). In addition to these conventional tests, the new cultures were also characterized with respect to their polar lipids, their deoxyribonucleic acid (DNA) base ratio values (mole percent of guanine plus cytosine) and their straight chain fatty acid composition.

The main general properties of the four new bacterial strains are that they:
1. Are strictly aerobic;
2. Are gram negative;
3. Are non-pigmented;
4. Do not form spores;
5. Are slender rods;
6. Are motile;
7. Grow very well on methanol;
8. Do not grow on methane;
9. Grow on methylamine, but not formate, trimethylamine or ethanolamine;
10. Grow poorly on glucose;
11. Exhibit the ribulose monophosphate pathway of carbon assimilation;
12. Have $Q_8$ as their major ubiquinone component;
13. Have as their predominant fatty acid a straight chain fatty acid containing 16 carbon atoms;
14. Exhibit an optimum temperature for growth between 37° and 42° C.;
15. Have a maximum temperature for growth of 44° C.;
16. Are oxidase positive;
17. Are catalase positive;
18. Have no vitamin requirement for growth;
19. Cannot grow on the following carbon sources: L-rhamnose, D-fucose, L-sorbose, D-mannose, cellobiose, starch, inositol, erythritol, succinate (Na), adipic acid, 2-oxoglutarate, D,L-lactate (Na), D,L-malate (Na), D-tartrate (Na), propionate (Na), D-laevulinate (Na), pelargonate (Na), citrate (Na), citraconate (Na), saccharic acid, D,L-arginine, L-alanine, L-valine, L-leucine, glycine, L-histidine, D,L-phenylalanine, L-proline, ethanol, propylene glycol, 2,3-butylene glycol, geraniol, trimethylamine, trimethylamine N-oxide, ethylamine, ethanolamine, butylamine, tryptamine, putrescine, betaine, sarcosine and phenol.
20. Utilize the following nitrogen sources: ammonium nitrate, ammonium sulphate, ammonium chloride and urea.
21. Are sensitive to the following antibiotics: chlorotetracycline, furazolidone, neomycin, streptomycin, oxytetracycline, gentamycin, colistin sulphate, ampicillin, carbenicillin, co-trimoxazole, kanamycin and tetracycline.
22. Are resistant to chloramphenicol, penicillin G and cephalothin 30.
23. Lack the following enzymatic activities: extra-cellular DNase, O-nitrophenyl-beta-d-galactosidase, arginine hydrolase, lysine decarboxylase, ornithine decarboxylase, tryptophan deaminase, trypsin, chymotrypsin, phosphoamidase, alpha-galactosidase, beta-glucuronidase, alpha-glucosidase, N-acetyl-beta-glucosaminidase, alpha-mannosidase and alpha-fucosidase.
24. Have the following enzymatic activities: alkaline phosphatase, butyrate esterase, caprylate esterase lipase, myristate lipase, leucine arylamidase, valine arylamidase, acid phosphatase and beta-glucosidase.
25. Cannot grow on nutrient broth, Maconkey's agar, salmonella-shigella agar or Jordan tartrate agar.
26. Have scant growth on nutrient agar.
27. Have no activity in the following biochemical tests: production of indole, production of $H_2S$, reaction on methyl red, urea hydrolysis or gelatin hydrolysis.
28. A mole percent of guanine plus cytosine in the range of 50.5–59.05%.

TABLE 1

| | KISRI 5 (NCIB 12135) | KISRI 6.1 (NCIB 12136) | KISRI 512 (NCIB 12137) | KISRI 5112 (NCIB 12138) |
|---|---|---|---|---|
| Cultural Characteristics on Solid Media: | | | | |
| Shape | Circular | Irregular | Circular | Circular |
| Diameter (mm) | 2.0 | 2.0 | 1.5 | 2.0 |
| Chromogenesis | Absent | Absent | Absent | Absent |
| Opacity | Opaque | Opaque | Opaque | Opaque |
| Elevation | Convex | Convex | Convex | Convex |
| Surface | Smooth | Rough | Glistening | Smooth |
| Edge | Entire | Undulate | Entire | Entire |
| Consistency | Butyrous | Granular | Butyrous | Butyrous |
| Growth on Carbon Source:* | | | | |
| Methanol | ++ | ++ | ++ | ++ |
| Methylamine | + | + | + | + |
| Dimethylglycine | − | + | − | + |
| Glucosamine | − | − | ± | − |
| n-Butanol | + | − | − | + |

TABLE 1-continued

|  | KISRI 5 (NCIB 12135) | KISRI 6.1 (NCIB 12136) | KISRI 512 (NCIB 12137) | KISRI 5112 (NCIB 12138) |
| --- | --- | --- | --- | --- |
| Fructose | ± | − | ± | ± |
| Glucose | ± | ± | ± | ± |
| Galactose | − | − | ± | ± |
| Sucrose | − | − | − | ± |
| Trehalose | − | − | − | ± |
| Maltose | − | − | − | ± |
| Sensitivity to Antibiotics:** | | | | |
| Cephaloridine | − | + | − | − |
| Novobiocine | − | + | + | + |
| Sulfanomide | + | − | − | + |
| Utilization of Nitrate Nitrogen | + | − | + | + |
| Reduction of Nitrate to Nitrite | + | − | − | − |
| Production of AMC*** | + | − | − | − |
| Cell Constituents: | | | | |
| Polar Lipids**** | PE + PG | PG + PC | PE | PG |
| Guanine + cytosine % | 52.90 | 59.05 | 50.51 | 51.12 |

*"±" Indicates weak growth
**"−" indicates antiobiotic resistant, "+" indicates antibiotic sensitive,
***AMC = Acetyl Methyl Carbinol
****PG = Phosphatidyl glycerol; PE = Phosphatidyl ethanolamine; PC = Phosphatidyl Choline The four new strains exhibit many similar characteristics as shown above. However, there are also some differences between the four KISR strains as shown in Table 1. The characteristics that differentiate them from each other and from other Methylophilus strains can be summarized as follows:

a) Strain KISRI 5 (NCIB 12135). This strain grows well on methanol, methylamine and n-butanol. It grows slowly and weakly on fructose and glucose and is resistant to cephaloridine and novobiocine. It utilizes nitrate nitrogen, and it can reduce nitrate to nitrite and produce acetyl methylcarbinol. This strain contains the polar lipids phosphatidyl ethanolamine (PE) and phosphatidyl glycerol (PG). Its mole percent of guanine plus cytosine is 52.90%.

b) Strain KISRI 6.1 (NCIB 12136). It grows well on methanol, methylamine and dimethylglycine. It has irregular, rough, undulate colonies, flocculant in broth. It grows slowly on glucose and does not grow at all on other sugars. This strain is sensitive to cephaloridine and novobiocine. It cannot utilize nitrate nitrogen. It contains the polar lipids phosphatidyl glycerol (PG) and phosphatidyl choline (PC), and its mole percent of guanine plus cytosine is 59.05%.

c) Strain KISRI 512 (NCIB 12137). This strain grows well on methanol and methylamine. It grows slowly on glucose, galactose, fructose and glucosamine. It is resistant to cephaloridine and sulfanomide, but it is sensitive to novobiocine. This strain can utilize nitrate nitrogen and contains only the polar lipid phosphatidyl ethanolamine (PE). Its mole percent of guanine plus cytosine is 50.51%.

d) Strain KISRI 5112 (NCIB 12138). This strain grows well on methanol, methylamine, dimethylglycine and n-butanol, and it grows slowly on many other carbon sources such as fructose, galactose, sucrose, trehalose, maltose and glucose. It is resistant to cephaloridine but is sensitive to novo-biocine and sulfanomide. It contains only one polar lipid which is phosphatidyl glycerol (PG). Its mole percent of guanine plus cytosine is 51.12%.

None of the four KISR strains belongs to the family Methylomonodaceae which comprises the two genera Methylomonas, which comprises strains that utilize either methane or mixtures of methane and methanol, and Methylococcus, which comprises strains with coccoidal cells (Kreig & Holt, *Bergey's Manual of Systematic Bacteriology*, Vol. 1, pp. 259–260 (Williams and Wilkins 1984). The four KISR cultures are non-methane utilizers, and have three properties in common with the obligate methylotrophs, namely: (1) $Q_8$ as their major ubiquinone system; (2) the predominant straight chain fatty acid contains 16 carbon atoms; and (3) a mole percent of guanine plus cytosine in the range of 49.8–59.0%. Since the KISR strains grow slowly on multi-carbon sources, they could be considered as type M restricted facultative methylotrophs that are classified with obligate methylotrophs (Anthony, C., *The Biochemistry of the Methylotrophs*, p. 24 (Academic Press 1982).

There are three known species of type M restricted facultative methylotrophs: *Methylophilus methylotrophus* (NCIB 10515), *Methylobacillus glycogens* (NCIB 11375) and *Methylomonas clara* (ATCC 31226). Whereas *M. clara* utilizes both methane and methanol, none of the four KISR strains can utilize methane. Whereas *M. glycogens* is a bacillus and has three types of polar lipids, all four of the KISR strains are rods and have only one or two types of polar lipids. Three of the KISR strains contain different types of polar lipids than does *M. methylotrophus*. The fourth KISR strain has a different mole percentage guanine plus cytosine than does *M. methylotrophus*, and it is sensitive to the antibiotics cephaloridine and gentamycin whereas *M. methylotrophus* is not. Based on these differences, it is claimed that each of the four KISR strains is a new species of the genus Methylophilus.

The constituents of the culture medium play a very important role in determining the quality and quantity of the bacterial cells that are produced in it. An optimized culture medium can, to a large extent, be genus or even strain specific. Microbiological growth media which are formulated for the growth of microorganisms in shake flasks or on plates in which a means of controlling process operating parameters, particularly pH, is absent. Thus, such media are inevitably heavily buffered. In continuous flow fermentation, however, pH is generally controlled externally, and a heavily buffered medium is not required or desired since excessive buffering of growth media can adversely affect the availabilities of essential inorganic nutrients and gives a high concentration of ions. This high concentration of ions, in turn, affects trans-membrane transfer mechanisms in microorganisms, thereby increasing permeability of the membrane and reducing the retention of valuable organic intracellular compounds in the growing microbial cells.

A culture medium has been discovered which allows for the efficient and optimal growth of all of the new bacterial strains of the invention on methanol as the carbon source and in continuous flow chemostat culture conditions. Use of this medium eliminates excessive buffering and high ionic strength and minimizes foam production. The use of this culture medium to grow one or more of the novel strains of Methylophilus of the invention gives optimum production of single cell protein and is appropriate for use in industrial-scale fermentations. Bacterial cells are produced rapidly at high concentrations and with a high feedstock conversion efficiency by cultivating any of the four novel Methylophilus strains of the invention in the optimized medium. The resultant single cell protein has a high protein content and can be used to enrich the nutritive value of animal, poultry and fish feeds.

The optimized culture medium of the invention is an aqueous medium comprising methanol and the following components in milligrams per gram of methanol used: phosphorus, 15; potassium, 15; magnesium, 4.0; calcium, 0.75; sodium, 0.39; iron, 0.3; copper, 0.01; zinc, 0.01; manganese, 0.05; molybdenum, 0.02; cobalt, 0.02; boron, 0.02; nickel, 0.01; ethylenediaminetetra acetic acid (EDTA), 5.0. This collection of components, including the EDTA, will be referred to herein as "mineral nutrients." Variations in the amounts used of individual components of up to plus or minus 20 percent of the stated values provides an entirely effective medium. Table 2 shows the preferred sources of the elements used to formulate the medium. The requirement for nitrogen is met by using a 6% solution of ammonia to adjust the pH to about 6.8.

Under batch mode, Strains KISRI 5 (NCIB 12135) and KISRI 512 (NCIB 12137) show the best growth at a concentration of from about 5 to about 20 grams of methanol per liter, and are preferably cultured using 20 grams per liter of methanol; while Strains KISRI 6.1 (NCIB 12136) and KISRI 5112 (NCIB 12138) show the best growth at a methanol concentration of from about 5 to about 10 grams per liter, and are preferably cultured at 10 grams per liter of methanol.

In addition to having an efficient bacterial strain and an optimized growth medium, it is also essential to have an efficient mode of overall process operation if a process for the production of single cell protein is to be of maximum economic potential. Most important in this respect is minimization of the volume of materials that flow into the overall process.

TABLE 2

| Medium Component and Preferred Source of The Component | Mg Of Component Per Gram Methanol |
| --- | --- |
| Phosphorus (as $H_3PO_4$) | 15.00 |
| Potassium (as $K_2SO_4$) | 15.00 |
| Magnesium (as $MgSO_4.7H_2O$) | 4.00 |
| Calcium (as $CaCl_2.2H_2O$) | 0.75 |
| Sodium (as NaCl) | 0.39 |
| Iron (as $FeSO_4.7H_2O$) | 0.30 |
| Copper (as $CuSO_4.5H_2O$) | 0.01 |
| Zinc (as $ZnSO_4.7H_2O$) | 0.01 |
| Manganese (as $MnSO_4.4H_2O$) | 0.05 |
| Molybdenum (as $Na_2MoO_4.2H_2O$) | 0.02 |
| Cobalt (as $CoCl_2.6H_2O$) | 0.02 |
| Nickel (as $NiSO_4.6H_2O$) | 0.01 |
| Boron (as $H_3BO_4$) | 0.02 |
| Ethylenediaminetetraacetic acid (EDTA) | 5.00 |

Figure 2:
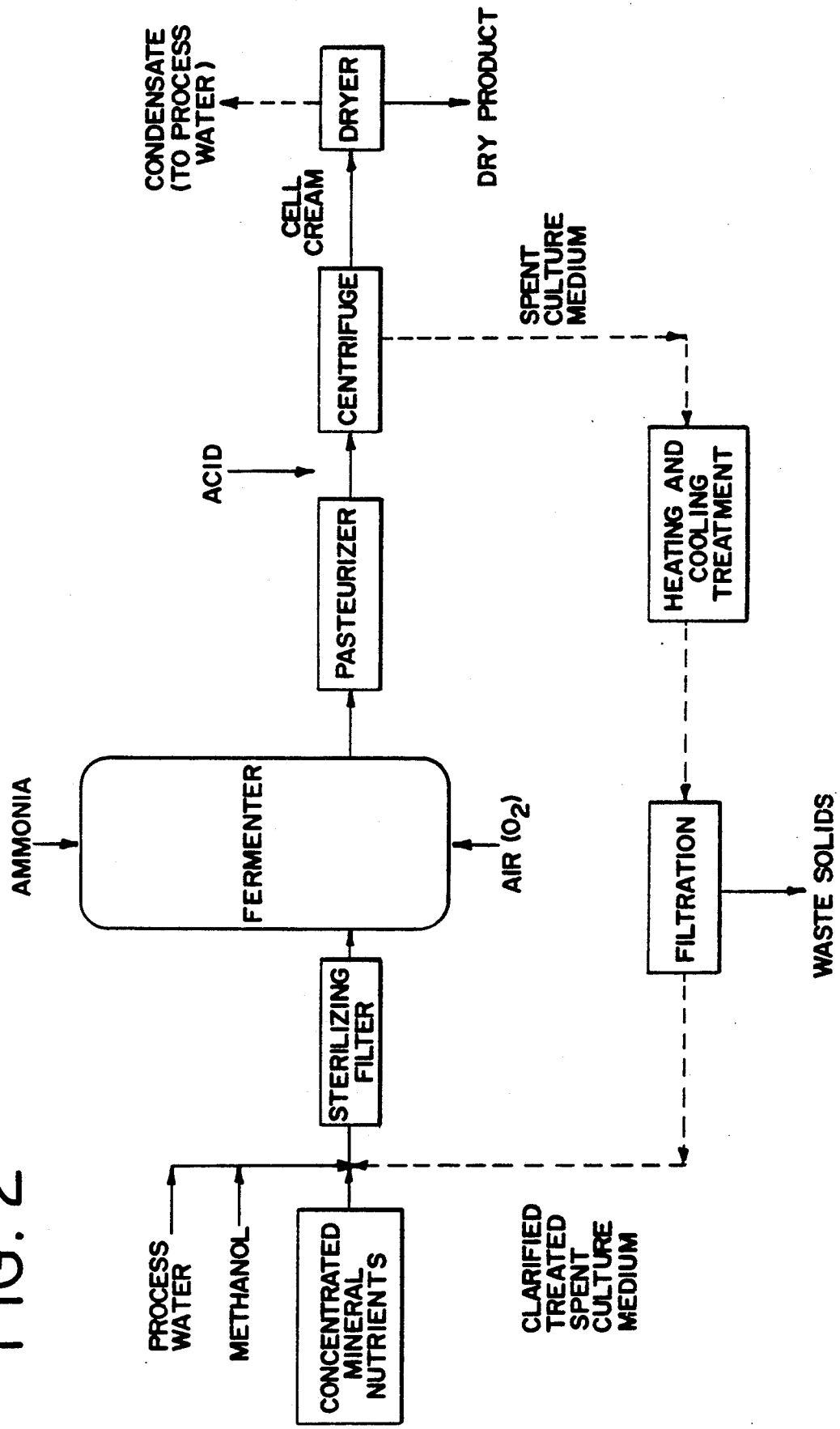
FIG. 2 depicts, in flow-chart form, a second embodiment of the method of the invention.

Particularly in hot, arid regions, the volume of water of drinking quality used must be kept to a minimum since such water is both scarce and expensive in these areas. Consequently, a method for overall process operation which involves continuously collecting and recycling spent culture medium has been developed. The spent culture medium is separated from the microorganisms in the culture by centrifuging the effluent from the fermenter. The addition of acid to the fermenter effluent prior to the centrifugation causes flocculation of the cells and better separation. After centrifugation, the spent culture medium is heated to from about 83° to about 87° C., preferably to about 85° C., is then cooled to from about 40° to about 50° C. to precipitate biopolymeric matter and is next continuously filtered to remove the precipitated biopolymeric matter. After filtration, the required mineral nutrients are metered into the clarified spent culture medium to adjust the concentration of the mineral nutrients to those listed in Table 2. The spent culture medium, supplemented with necessary mineral nutrients, is then filtered sterilized and supplied to the fermenter, alone or along with fresh mineral nutrients, as a separate stream in the case where separate streams of mineral nutrients, methanol and fresh process water are employed. The spent culture medium adjusted to the proper concentrations of mineral nutrients can also be supplemented with methanol and fresh process water to prepare complete culture medium which is then filter sterilized. In this case, the complete culture medium prepared from the spent culture medium is added to the fermenter, alone or along with fresh complete culture medium, in one stream. These two variants of the process of the invention are illustrated in FIGS. 1 and 2 which are discussed in greater detail below. The recycling of spent culture medium reduces the use of mineral nutrients and water, thereby increasing the efficiency and decreasing the cost of the process.

FIGS. 1 and 2 illustrate, in flow chart form, two variants of the method of the invention as it would operate in the continuous flow mode. As noted above, FIG. 1 illustrates an embodiment of the method in which the water, methanol and mineral nutrients are supplied to the fermenter in separate streams, whereas FIG. 2 illustrates an embodiment in which the water, methanol and mineral nutrients are first mixed to prepare complete culture medium and the complete culture medium is added to the fermenter in a single stream. With respect to both embodiments, the mineral nutrients are used in the form of a concentrate wherein the amounts of the minerals are chosen so that when the concentrated mineral nutrients are mixed with the water and methanol, the final culture medium has the concentration of mineral nutrients given above in Table 2.

The fermenter is an impeller-agitated fermenter which can be sparged with air at selected flow rates. The fermenter is further equipped with a means for the addition and removal of medium, with a dissolved oxygen measurement probe, a pH measurement probe and control system, a foam control system and a temperature probe and control system.

In practicing the embodiments of the method of the invention illustrated in FIGS. 1 and 2, an appropriate amount of filter sterilized medium is placed in the fermenter which has already been inoculated with one of the Methylophilus strains of the invention. During growth, filter-sterilized air is sparged through the culture medium, the pH is maintained at 6.8 by the addition of a 6% solution of ammonia, and the temperature is preferably maintained at 40° C. ±2°. To ensure that the dissolved oxygen concentration is maintained above 1.25 ppm, the impeller speed is increased as the fermentation proceeds. Foam production is controlled by the automatic addition of a sterilized antifoam agent, triggered by a foam detecting probe in the fermenter head space.

In practicing the methods illustrated in FIGS. 1 and 2, the fermenter is converted to continuous flow operation when a significant cell density is reached. The effluent produced during steady state operation is pasteurized and then acidified to flocculate the cells. The spent culture medium is next clarified by centrifugation, and the clarified spent culture medium is heated to from about 83° to about 87° C., followed by cooling to from about 40° to about 50° C. which causes the precipitation of biopolymeric matter. The precipitated biopolymeric matter is removed by filtration, and the elemental composition of the filtered clarified spent medium is analyzed and supplemented with mineral nutrients. The supplemented spent medium is added to the supply of concentrated mineral nutrients, or is used alone as the source of mineral nutrients, for the preparation of additional culture medium for use in the fermenter.

The cell cream containing the microorganisms which was separated from the culture medium by the first centrifugation is washed and dried. The condensate formed during the drying operation can be recycled and used as a source of water. The dried microorganisms may be further processed to extract proteinaceous material.

The following examples further illustrate the scope of the present invention.

EXAMPLE 1

The four novel methanol utilizing bacteria, Methylophilus KISRI 5 (NCIB 12135), Methylophilus KISRI 6.1 (NCIB 12136), Methylophilus KISRI 512 (NCIB 12137) and Methylophilus KISRI 5112 (NCIB 12138), were separately grown using the optimum medium (Table 2) containing 5 grams per liter of methanol and appropriate amounts of mineral nutrients. Growth was carried out in a 7 liter nominal volume, impeller-agitated fermenter which could be sparged with air at selected flow rates. The fermenter was further equipped with a dissolved oxygen measurement probe, a pH measurement probe and control system, a foam control system and a temperature control system. To the fermenter, 3.6 liters of the medium, without methanol, was added. The medium was then sterilized, in situ, for 45 minutes at 121° C. After cooling to 40° C., enough filter-sterilized methanol to give an initial concentration of 5 grams per liter, and 400 milliliters of actively growing inoculum of the appropriate novel culture to be tested were added to the fermenter. During growth, sterilized air was sparged through the culture medium, the pH was maintained at 6.8 by the addition of a 6% solution of ammonia, and the temperature was maintained at 40° C.±2°. To ensure that the dissolved oxygen concentration was maintained above 1.25 ppm, the impeller speed was increased as the fermentation proceeded. Foam production was controlled by automatic addition of a sterilized silicone based anti-foam agent, triggered by a foam detecting probe in the fermenter head space.

The culture medium was sampled aseptically at intervals and the cell density was measured spectrophotometricly at a wavelength of 620 nm. For each novel strain, the doubling time was measured, and the maximum specific growth rate constant was calculated. The specific growth rate constants were:

0.48 $h^{-1}$ for Methylophilus KISRI 5 (NCIB 12135);
0.48 $h^{-1}$ for Methylophilus KISRI 6.1 (NCIB 12136);
0.46 $h^{-1}$ for Methylophilus KISRI 512 (NCIB 12137); and
0.46 $h^{-1}$ for Methylophilus KISRI 5112 (NCIB 12138).

EXAMPLE 2

The four novel methanol utilizing bacteria, Methylophilus KISRI 5 (NCIB 12135), Methylophilus KISRI 6.1 (NCIB 12136), Methylophilus KISRI 512 (NCIB 12137 and Methylophilus KISRI 5112 (NCIB 12138), were separately grown using the optimized medium (Table 2) containing 5 grams per liter of methanol and appropriate amounts of mineral nutrients. Growth was carried out in a 7 liter nominal volume, impeller-agitated fermenter which could be sparged with air at selected flow rates. The fermenter was further equipped with means for the addition and removal of medium, with a dissolved oxygen measurement probe, a pH measurement probe and control system, a foam control system and a temperature probe and control system. First, 3.6 liters of the medium without methanol was placed in the fermenter and sterilized in situ at 121° C. for 45 minutes. After cooling to 40° C., enough filter-sterilized methanol to give an initial concentration of 5 grams per liter and 400 millileters of actively growing inoculum were added to the fermenter. During growth, filter-sterilized air was sparged through the culture medium, the pH was maintained at 6.8 by the addition of a 6% solution of ammonia, and the temperature was maintained at 40° C.±2°. To ensure that the dissolved oxygen concentration was maintained above 1.25 ppm, the impeller speed was increased as the fermentation proceeded. Foam production was controlled by the automatic addition of a sterilized silicone based anti-foam agent, triggered by a foam detecting probe in the fermenter head space.

When a significant cell density was reached, the fermenter was converted to continuous flow operation using the culture medium formulation given in Table 2 containing 10 grams per liter of methanol and appropriate amounts of mineral nutrients at a flow rate such that the hydraulic residence time was 5 hours. A steady state, with the rate of methanol supply restricting growth, was achieved for all four of the novel KISR strains after eight volume changes in the fermenter. Other parameters were maintained at the level existing at batch start up.

While operating under steady state conditions, samples of the fermentation broth were collected under chilled conditions. The fermentation borth were collected was centrifuged, and both supernatant and cell cream were collected. The methanol concentration in both the collected supernatant and the medium feed was determined to ascertain the amount of methanol consumed. The cell cream was used to determine cell density on a dry weight basis and to calculate the methanol based biomass yield coefficient. Additional washed and freeze dried cells were analyzed for crude protein, nucleic acid content, total amino acid content and individual amino acid composition. The results of these analyses, together with the methanol based biomass yield coefficient are given in Table 3 for the four novel KISR bacteria.

TABLE 3

|  | KISRI-5 (NCIB 12135) | KISRI-6.1 (NCIB 12136) | KISRI-512 (NCIB 12137) | KISRI-5112 (NCIB 12138) |
|---|---|---|---|---|
| Methanol based biomass yield coefficient (g.g$^{-1}$) | 00.420 | 00.430 | 00.430 | 00.440 |
| *Crude Protein (%) | 84.300 | 84.600 | 85.000 | 83.100 |
| *Nucleic acid (%) | 10.400 | 11.500 | 09.990 | 10.360 |
| *Total amino acids (%) | 60.400 | 62.100 | 58.000 | 59.800 |
| Aspartic acid | 07.960 | 08.510 | 08.450 | 08.112 |
| Threonine | 02.372 | 02.630 | 03.150 | 02.370 |
| Serine | 02.770 | 02.720 | 02.640 | 02.590 |
| Glutamic acid | 07.130 | 07.740 | 07.100 | 07.100 |
| Proline | 05.112 | 04.560 | 02.830 | 05.530 |
| Cysteine | 00.740 | 00.650 | 00.150 | 00.690 |
| Glycine | 03.600 | 02.390 | 03.800 | 03.790 |
| Alanine | 05.450 | 05.610 | 05.230 | 05.450 |
| Valine | 03.164 | 02.840 | 02.910 | 02.980 |
| Methionine | 00.516 | 00.366 | 00.060 | 00.390 |
| Isoleucine | 01.790 | 01.940 | 02.060 | 01.710 |
| Leucine | 04.830 | 04.910 | 05.060 | 04.830 |
| Tyrosine | 02.890 | 03.110 | 02.850 | 02.930 |
| Phenylalanine | 02.570 | 02.820 | 02.790 | 02.790 |
| Histidine | 01.296 | 01.350 | 01.170 | 01.240 |
| Lysine | 03.940 | 04.190 | 04.270 | 03.800 |
| Arginine | 03.110 | 03.182 | 03.400 | 02.900 |

*Values are corrected for moisture content.

EXAMPLE 3

The novel methanol utilizing bacterium Methylophilus KISRI 5 (NCIB 12135) was grown as described in Example 2, with the exception that the effluent produced during steady state operation was collected under chilled conditions. Some 60 liters of the spent chilled culture medium was acidified with phosphoric acid ($H_3PO_4$) to flocculate the cells, and the culture medium was then clarified by centrifugation. The clarified spent culture medium was heated to 85° C. and then cooled to 40°–50° C. which caused the precipitation of biopolymeric matter. The precipitated biopolymeric matter was removed by filtration through a 0.1–0.5 mm mesh stainless steel filter.

The elemental composition of the clarified spent medium was analyzed and supplemented to give the same elemental composition appropriate for 10 grams per liter of methanol as listed in Table 2. After addition of 10 grams per liter of methanol, the spent medium was filter sterilized and used in place of fresh medium for culturing additional KISRI 5 (NCIB 12135) operating under the same conditions as described in Example 2 (batch mode and continuous mode). The results are given in Table 4.

TABLE 4

|  | Fresh Medium | Recycled Medium |
|---|---|---|
| Batch Fermentation Mode |  |  |
| Maximum specific growth rate constant | 0.49 | 0.49 |
| Continuous Fermentation Mode |  |  |
| Methanol base biomass yield coefficient (g.g$^{-1}$) | 0.42 | 0.41 |
| *Crude protein (%) | 84.70 | 83.70 |
| *Total amino acids (%) | 60.35 | 62.50 |
| *Nucleic acids (%) | 11.50 | 10.50 |

*On dry weight basis

EXAMPLE 4

The culture of bacterial cells on the pilot plant scale was undertaken using, in separate experiments, Methylophilus KISRI 5 (NCIB 12135) and Methylophilus KISRI 6.1 (NCIB 12136). The pilot plant fermenter had a nominal volume of 1500 liters and a liquid working volume of 800 liters. It was equipped with the following process operations: intermittent medium preparation, continuous (multi-stream) medium sterilization, continuous flocculation and pasteurization, continuous centrifugation and continuous drying of the thickened cell cream. The pilot fermenter was provided with similar operation and control facilities to those described for the continuous flow seven liter fermenter described in Example 2. The composite continuous culture medium used was the optimized medium described in Table 2 containing 20 grams per liter of methanol and appropriate amounts of mineral nutrients. For the growth of either bacterium, the temperature was maintained at 40° C. ±2° C., and a hydraulic residence time in the fermenter of 10 hours was employed. Prior to batch start up, the fermenter was inoculated with 15 liters of an inoculum of the appropriate active culture.

Over 150 kg of dry single cell protein was produced and was subjected to microbiological quality control analyses, chemical analyses, nutritional evaluation and sub-chronic toxicological testing. The microbiological quality control tests at no time showed the presence of any pathogenic microorganisms, and the single cell protein produced met the international standard for microbiological testing. The results of the chemical analysis of the single cell protein produced by Methylophilus KISRI 5 (NCIB 12135) and Methylophilus KISRI 6.1 (NCIB 12136) are shown in Table 5. The single cell protein was tested for subchronic oral toxicity for 13 weeks in rats by the well-known, highly-reputed International Toxicological Institute (TNO, P.O. Box 360, Zeist, The Netherlands). The results of this study showed that the feeding of the single cell protein produced by both KISRI 5 (NCIB 12135) and KISRI 6.1 (NCIB 12136) to rats at levels up to 30% of their total diet failed to induce any obvious deleterious effects.

TABLE 5

|  | KISRI 5 (NCIB 12135) | KISRI 6.1 (NCIB 12136) |
|---|---|---|
| Crude Protein* | 82.4% | 77.00% |
| Fat | 5.9% | 4.20% |
| Dietary fiber | 0.4% | 0.20% |
| Ash | 9.8% | 11.30% |
| Calcium | 0.2% | 0.26% |
| Phosphorus | 1.9% | 2.70% |
| Sodium | 0.2% | 0.20% |
| Potassium | 1.4% | 1.90% |

TABLE 5-continued

|  | KISRI 5 (NCIB 12135) | KISRI 6.1 (NCIB 12136) |
| --- | --- | --- |
| Magnesium | 0.5% | 0.63% |
| Iron | 480 ppm | 1200 ppm |
| Copper | 20 ppm | 27 ppm |
| Manganese | 105 ppm | 15 ppm |
| Zinc | 105 ppm | 85 ppm |
| Cobalt | 40 ppm | 55 ppm |
| Chromium | 1.5 ppm | 2.0 ppm |
| Tin | <1 ppm | <1 ppm |
| Selenium | 0.04 ppm | 0.04 ppm |
| Iodine | 0.7 ppm | 0.6 ppm |
| Choline | 550 ppm | 600 ppm |

*On dry weight basis

We claim:

1. A purified and isolated methanol-utilizing bacterium selected from the group consisting of Methylophilus KISRI 5 (NCIB 12135), Methylophilus KISRI 6.1 (NCIB 12136), Methylophilus KISRI 512 (NCIB 12137), Methylophilus. KISRI 5112 (NCIB 12138).

2. A biologically pure bacterial culture comprising:
   one bacterium selected from the group consisting of Methylophilus KISRI 5 (NCIB 12135), Methylophilus KISRI 6.1 (NCIB 12136), Methylophilus KISRI 512 (NCIB 12137), Methylophilus KISRI 5112 (NCIB 12138), and
   a methanol-containing aqueous culture medium.

3. A biologically pure bacterial culture comprising:
   two or more bacteria selected from the group consisting of Methylophilus KISRI 5 (NCIB 12135), Methylophilus KISRI 6.1 (NCIB 12136), Methylophilus KISRI 512 (NCIB 12137), Methylophilus KISRI 5112 (NCIB 12138); and
   a methanol-containing aqueous culture medium.

4. The bacterial culture of either claim 2 or claim 3 wherein the culture medium comprises:
   from about 12 to about 18 mg phosphorous;
   from about 12 to about 18 mg potassium;
   from about 3.2 to about 4.8 mg magnesium;
   from about 0.60 to about 0.90 mg calcium;
   from about 0.31 to about 0.47 mg sodium;
   from about 0.24 to about 0.36 mg iron;
   from about 0.008 to about 0.012 mg copper;
   from about 0.008 to about 0.012 mg zinc;
   from about 0.04 to about 0.06 mg manganese;
   from about 0.016 to about 0.024 mg molybdenum;
   from about 0.016 to about 0.024 mg cobalt;
   from about 0.016 to about 0.024 mg boron;
   from about 0.008 to about 0.012 mg nickel; and
   from about 4.00 to about 6.00 mg ethylene diaminetetraacetic acid;
   per gram of methanol.

* * * * *

UNITED STATES PATENT AND TRADEMARK OFFICE
CERTIFICATE OF CORRECTION

PATENT NO. : 5,314,820
DATED : May 24, 1994
INVENTOR(S) : Ibrahim Y. Hamdan et al.

It is certified that error appears in the above-indentified patent and that said Letters Patent is hereby corrected as shown below:

Column 1, line 25, delete "production" and substitute --introduction--.

Column 1, line 60, delete "methylophilus" and substitute --Methylophilus--.

Column 3, line 26, delete "eachcategory" and substitute --each category--.

Column 9, line 67, delete "in situ" and substitute --*in situ*--.

Column 10, line 3, delete "inocolum" and substitute --inoculum--.

Column 10, lines 15-16 delete "spectrophotom-etricly" and substitute --spectrophotometrically--.

Column 10, line 43, delete "in situ" and substitute --*in situ*--.

UNITED STATES PATENT AND TRADEMARK OFFICE
CERTIFICATE OF CORRECTION

PATENT NO. : 5,314,820
DATED     : May 24, 1994
INVENTOR(S): Ibrahim Y. Hamdan et al.

It is certified that error appears in the above-indentified patent and that said Letters Patent is hereby corrected as shown below:

Column 10, line 46, delete "millileters" and substitute --milliliters--.

Column 11, lines 3-4, delete "borth were collected" and substitute --broth--.

Column 13, claim 1, line 21, after "Methylophilus" delete ".".

Column 13, claim 2, line 27, after "(NCIB 12138)" delete ",".

Signed and Sealed this

Fourth Day of April, 1995

Attest:

BRUCE LEHMAN

*Attesting Officer*   *Commissioner of Patents and Trademarks*